US006441011B1

(12) United States Patent
Susilo et al.

(10) Patent No.: US 6,441,011 B1
(45) Date of Patent: Aug. 27, 2002

(54) COMBINED PREPARATION CONSISTING OF 2-METHYLTHIAZOLIDINE-2,4-DICARBOXYLIC ACID AND PARACETAMOL

(75) Inventors: Rudy Susilo, Münstereifelerstr. 39, 50937 Köhn; Hans Rommelspacher, Berlin, both of (DE); Lidia Wlodek, Krokow (PL)

(73) Assignee: Rudy Susilo, Cologne (DE)

( * ) Notice: Subject to any disclaimer, the term of this patent is extended or adjusted under 35 U.S.C. 154(b) by 0 days.

(21) Appl. No.: 09/380,472

(22) PCT Filed: Feb. 24, 1998

(86) PCT No.: PCT/DE98/00583

§ 371 (c)(1),
(2), (4) Date: Nov. 8, 1999

(87) PCT Pub. No.: WO98/38994

PCT Pub. Date: Sep. 11, 1998

(30) Foreign Application Priority Data

Mar. 3, 1997 (DE) ......................................... 197 11 053

(51) Int. Cl.⁷ ..................... A61K 31/135; A61K 31/425
(52) U.S. Cl. ...................................................... 514/369
(58) Field of Search .......................................... 514/369

(56) References Cited

U.S. PATENT DOCUMENTS

| | | | | |
|---|---|---|---|---|
| 4,335,210 A | * | 6/1982 | Meister et al. | 435/113 |
| 4,434,158 A | * | 2/1984 | Meister et al. | 424/94 |
| 4,438,124 A | * | 3/1984 | Meister et al. | 424/270 |
| 4,567,192 A | * | 1/1986 | Revesz et al. | 514/369 |
| 4,647,571 A | * | 3/1987 | Meister et al. | 514/369 |
| 4,839,387 A | * | 6/1989 | Poli | 514/17 |
| 4,868,114 A | * | 9/1989 | Nagasawa et al. | |

FOREIGN PATENT DOCUMENTS

| | | | |
|---|---|---|---|
| DE | 2116629 | | 10/1972 |
| GB | 1583602 | * | 1/1981 |
| WO | 98 38 994 | * | 9/1998 |

OTHER PUBLICATIONS

Nagasawa et al (II) J. Biochem Toxicol. 11(6) :289–295 (1996) 1997.*
Nagasawa et al J. Med. Chem. 25(5): 489–491, 1982.*
Nagasawa et al J. Med. Chem. 27(5):591–596, 1984.*
Hazelton et al Jl. Pharmacol. & Exp. Ther. 237(1): 341–349, 1986.*
Rathbun et al Biochem. Pharmacol. 51(91: 1111–1116, 1996.*
Wlodek et al Fundam. Clin. Pharmacol. 11(5: 454–459, 1997.*
Wlodek et al Acta Biochem. Pol. 44(4):759–766, 1997.*
Schubert J. Biol. Chem. 114: 341–350, 1936.*
Wlodek and Rommelspachor Alcohol Alcoholism 29: 649–651, 1994.*
Nagasawa et al, "2–substituted thiazolidine–4(R)–carboxylic acids as prodrugs of L–cysteine. Protection of mice against actaminophen hepatotoxicity", J. Med. Chem., Bd. 27, 1984, Seiten 591–96.
Wlodek et al, "formation of 2–Methyl–thiazolidine–2,4–dicarboxylic acid from L–cysteine in rat tissues", Acta Biochimica Polonica, Bd. 31, 1984, Seiten 279–88.
Wlodek et al, "2–Methyl–thiazolidine–2,4–dicarboxylic acid protects against paracetamol induced toxicity in human liver derived HepG2 cells", Acta Biochimica Polonica, Bd. 44, Nr. 4, Oct. 1997, Seiten 759–66.

* cited by examiner

*Primary Examiner*—Shep K. Rose
(74) *Attorney, Agent, or Firm*—Wood, Philips, Katz, Clark & Mortimer

(57) ABSTRACT

This invention relates to a pharmaceutical containing a combination of 2-methyl-thiazolidine-2,4-dicarboxylic acid and paracetamol, and to the use of a combination of 2-methyl-thiazolidine-2,4-dicarboxylic acid and paracetamol as an analgesic and/or antipyretic.

15 Claims, No Drawings

COMBINED PREPARATION CONSISTING OF 2-METHYLTHIAZOLIDINE-2,4-DICARBOXYLIC ACID AND PARACETAMOL

This invention relates to a pharmaceutical that is characterized in that it contains a combination of 2-methyl-thiazolidine-2,4-dicarboxylic acid and paracetamol.

Long-term application and/or high doses of the widely used analgesic, paracetamol (acetaminophen), result in the destruction of hepatic and renal cells. The toxicity of paracetamol is caused by a chemically reactive metabolite, N-acetyl-p-benzochinonimine (NAPQI). This metabolite binds cell proteins such as enzymes that are thus deactivated. In addition, high doses of paracetamol increase the concentration of oxygen radicals, which results in the collapse of the cellular defense system against toxic influences. The degree to which cellular defense mechanisms are impaired, and cells destroyed, can be evaluated by measuring certain substances in the blood plasma as well as directly in the tissue. Examples of such indicator substances are lactate dehydrogenase (LDH), an enzyme, or the transaminases alanine-aminotransferase (AlAT), aspartate aminotransferase (AspT) in the blood serum as well as cysteine, cystine, malonyl dialdehyde, glutathione, accumulation of proteins containing sulfhydryl groups, and accumulation of smaller substances that also contain sulfhydryl groups.

The most widespread antidote to paracetamol poisoning is N-acetylcysteine. Compound preparations of paracetamol and N-acetylcysteine, however, are unknown. It is generally assumed that N-acetylcysteine is a low-toxic pharmaceutical. However, some barely known reports point to the fact that the toxicity risk N-acetylcysteine poses is underestimated (Estrela, J. M., Saez, G. T., Such, L. and Vina, J., Biochem. Pharmacol. 32:3483–3485 (1983), and Vina, J., Romero, F. J., Saez, G. T. and Pallardo, F. V., Experientia 39:164–165 (1983)). Researchers repeatedly tried to find alternatives because of the fact that N-acetyl cysteine can trigger toxic responses. It is absolutely improper to apply L-cysteine itself as this amino acid is highly toxic and causes the death of brain cells (Karlsen, R. L., Grofova, Y., Malthe-Sorensen, D. and Farnum, E., Exp. Brain. Res. 208:167–180 (1981)). This toxicity can be bypassed if a so-called prodrug is applied, i.e. a predecessor pharmaceutical from which the effective amino acid is released in a controlled way inside the body.

It is the problem of this invention to provide a compound preparation that is capable of reducing the cell toxicity of paracetamol, the proven analgesic and antipyretic.

This problem is solved according to the invention by providing a pharmaceutical that is characterized by containing a combination of 2-methyl thiazolidine-2,4-dicarboxylic acid and paracetamol as well as pharmaceutically harmless substrates, adjuvants and/or additives.

It was found, surprisingly, that 2-methyl-thiazolidine-2,4-dicarboxylic acid causes a reduction in the formation of free radicals and an increase in the concentration of sulfhydryl groups in the organism. Thus this compound has a cytoprotective and anti-inflammatory effect. This substance therefore is clearly superior to all compounds known as yet, e.g. N-acetylcysteine. Using 2-methyl thiazolidine-2,4-dicarboxylic acid can considerably reduce the toxic side-effects known from N-acetylcysteine.

Pyruvate, a completely harmless physiological substance, is formed as a by-product when L-cysteine is released from 2-methyl-thiazolidine-2,4-dicarboxylic acid. Unlike N-acetylcysteine, 2-methyl-thiazolidine-2,4-dicarboxylic acid is therefore very well tolerated. There are even indications that pyruvate has a protective effect (Rastellini, C., Cicalese, L., Zeevi, A., Mattes, C., Stauko, R. T., Starzl, T. E. and Rao, A. S., Transplant. Proceed. 27:3383–3384 (1995)). Pyruvate is physiologically formed from glucose and is needed in the tricarboxylic acid cycle for producing the cell's energy. It can therefore be expected that a slow enzymatic release of L-cysteine in the cells of the body has a retarding effect which would give rise to hope for a more lasting efficacy as compared to N-acetylcysteine.

Surprisingly, it was found that the treatment with a combination of 2-methyl-thiazolidine-2,4-dicarboxylic acid and paracetamol does not only prevent the destruction of the cellular defense system but also builds up a lasting efficacy of the mixture of 2-methyl thiazolidine-2,4-dicarboxylic acid and paracetamol. This points to an enzymatically controlled release of L-cysteine from 2-methyl-thiazolidine-2,4-dicarboxylic acid. Moreover, the findings after a monotherapy using a combination of 2-methyl-thiazolidine-2,4-dicarboxylic acid and paracetamol show that this substance is well tolerated by the liver.

The pharmaceuticals of the invention can be designed for oral, rectal, subcutaneous, intravenous or intramuscular administration.

The pharmaceuticals of the invent-ion are produced in a generally known way using the common solid or liquid substrates or diluents and the commonly used adjuvants of pharmaceutical engineering, their dosage depending on the intended application. Preferred preparations are forms of application suitable for oral administration. Such forms of application include tablets, film tablets, lozenges, capsules, pills, powder, solutions or suspensions, or depot systems.

Parenteral preparations such as injection solutions can also be taken into consideration, of course. Another example of suitable preparations is suppositories.

The respective tablets can be produced, for example, by intermixing the active ingredient with known adjuvants, e.g. inert diluents such as dextrose, sugar, sorbitol, mannite, polyvinylpyrrolidone, blasting agents such as corn starch or alginic acid, binding agents such as starch or gelatin, lubricants such as magnesium stearate or talc and/or agents for producing a depot effect such as carboxyl polymethylene, carboxylmethyl cellulose, cellulose acetate phthalate, or polyvinyl acetate. The tablets may also consist of multiple layers.

Accordingly, lozenges can be produced by coating the cores produced in a similar way as the tablets with agents that are typically used in lozenge coatings, e.g. polyvinylpyrrolidone or shellac, gum arabic, talc, titanium dioxide, or sugar. The lozenge coating may consist of multiple layers, and the adjuvants listed above for tablets can be used here as well.

Solutions or suspensions with the active agent of the invention may further contain sweetening agents such as saccharin, cyclamate or sugar as well as aromatizers such as vanillin or orange extract. They may further contain suspending agents such as sodium carboxymethyl cellulose or preservatives such as p-hydroxybenzoates. Capsules containing active ingredients can be produced, for example, by mixing the active agent with an inert carrier such as lactose or sorbitol and encapsulating it in gelatin capsules.

Suitable suppositories can be produced, for example, by intermixing with the respective substrates such as neutral fats or polyethylene glycol or their derivatives.

The examples below shall explain the invention in greater detail:

EXAMPLE 1

Determination of Time-dosage Dependency

Methods:

The interdependence of time and dosage of the combination of 2-methyl-thiazolidine-2,4-carboxylic acid (CP) and paracetamol (AA) was determined, first of all, under in-vivo conditions in mice; it was found that there are no toxic effects up to a dose of 2.4 mmol CP/kg of body weight. The mice were pre-treated using 1.2 mmol CP/kg, and 12 hours later they were treated with the control solution or 600 mg of paracetamol/kg of body weight i.p. Hepatic tissue and blood were extracted after another 3 hours, and the indicator substances were measured.

Findings:

The glutathione concentration in the hepatic tissue rose considerably within one hour post application from 1.2 or 2.4 mmol of 2-methyl-thiazolidine-2,4-dicarboxylic acid/kg of body weight. This increase could still be detected after 12 hours (Table 1). This lasting effect can be explained by the fact that an amino acid, L-cysteine, is released from 2-methyl-thiazolidine-2,4-dicarboxylic acid in the hepatic cell, and this amino acid is the decisive component of its defense system against toxic influences. Gluthatione contains L-cysteine and can be viewed as a natural depot form of L-cysteine.

A single dose of paracetamol (600 mg/kg of body weight) resulted in an enormous increase in enzymes in the blood serum that were released from the liver (AlAT, AspT) within 3 hours as a reflection of hepatic cell destruction. In addition, the concentration of oxygen radicals increased while the concentration of sulfhydryl groups, free cysteines and glycogen dropped dramatically (Table 2).

Pre-treatment with 2-methyl-thiazolidine-2,4-dicarboxylic acid (1.2 mmol/kg of body weight) suppressed the increase of hepatic enzymes in the serum and reduced the decrease in sulfhydryl groups. Cysteine and glycogen were significantly increased in the hepatic tissue. The formation of oxygen radicals was significantly reduced.

EXAMPLE 2

In-vitro Tests on Permanent Hepatic Cell Lines

The cytotoxicity of paracetamol and the protective action of 2-methyl-thiazolidine-2,4-dicarboxylic acid were tested on a permanent hepatic cell line (Hep G2 cells). The cells were kept for 10 days in a medium that contained paracetamol (1 mM). Another group of cells was treated in the same way in a medium that contained both paracetamol and 2-methyl-thiazolidine-2,4-dicarboxylic acid. The concentrations of the indicator substances were measured at the end of the period of exposure (Table 3). Treatment of Hep G2 cells with paracetamol (AA) resulted in an increase in free radicals which was prevented by simultaneous treatment with 2-methyl-thiazolidine-2,4-dicarboxylic acid (CP) (2 mM). L-cysteine and cystine concentrations dropped slightly after exposure to AA. This effect, too, was more than compensated by 2-methyl-thiazolidine-2,4-dicarboxylic acid. The concentrations of the other indicator substances remained unchanged under the conditions selected. It is therefore recommended to choose higher AA concentrations for later experiments.

The findings with the cell culture confirm the protective effect of 2-methyl-thiazolidine-2,4-dicarboxylic acid against high concentrations of paracetamol in the hepatic cell model.

TABLE 1

| Time after injection (h) | GSH µmol/g of wet weight | | | | |
|---|---|---|---|---|---|
| | Control 0.9% NaCl x ± SD | CP (1.2 mmol/kg) x ± SD | % of control | CP (2.4 mmol/kg) x ± SD | % of control |
| 1 | 6.45 ± 0.42 | 7.62$^b$ ± 0.37 | 117.5 | 8.27$^a$ ± 0.38 | 127.6 |
| 4 | 6.38 ± 0.25 | 5.56$^c$ ± 0.42 | 87.2 | 5.76 ± 0.42 | 90.3 |
| 8 | 5.97 ± 0.29 | 6.48 ± 0.67 | 108.5 | 6.69$^c$ ± 0.32 | 112.0 |
| 12 | 4.73 ± 0.31 | 5.77$^b$ ± 0.30 | 122.0 | 7.31$^a$ ± 0.41 | 154.5 |

TABLE 2

| No. | liver | Total SH | Non-protein SH | Protein SH | Cysteine | Cystine | Oxygen radicals | Glycogen mg/g wet weight of the liver | AlAT | AspAT units/l |
|---|---|---|---|---|---|---|---|---|---|---|
| | | | | µmol/g wet weight of the liver | | | | | | |
| 1. | Control (non fasted) 0.9% NaCl | 19.61$^a$ ± 0.16 | 6.19$^a$ ± 0.028 | 13.42 ± 0.15 | 0.201$^a$ ± 0.012 | 0.070$^a$ ± 0.004 | 0.131$^a$ ± 0.007 | 17.92$^a$ ± 0.16 | 35.2 | 155 |
| 2. | Control (fasted) 0.9% NaCl | 16.04 ± 0.16 | 3.84 ± 0.005 | 12.20 ± 0.14 | 0.199 ± 0.003 | 0.059 ± 0.004 | 0.177 ± 0.005 | 11.63 ± 0.53 | 22.6 | 127 |
| 3. | Paracetamol + 0.9% NaCl | 12.56$^a$ ± 0.12 | 0.22$^a$ ± 0.001 | 12.34 ± 0.20 | 0.062$^a$ ± 0.005 | 0.025$^a$ ± 0.008 | 0.317$^a$ ± 0.012 | 8.45$^a$ ± 0.16 | 682 | 855 |
| 4. | CP + 0.9% NaCl | 17.08$^a$ ± 0.19 | 3.81$^a$ ± 0.042 | 13.27 ± 0.16 | 0.240$^a$ ± 0.009 | 0.020$^a$ ± 0.006 | 0.120$^a$ ± 0.005 | 12.59 ± 0.21 | 20 | 199 |
| 5. | Paracetamol + CP | 16.34$^a$ ± 0.19 | 1.99$^a$ ± 0.022 | 14.35$^a$ ± 0.17 | 0.078$^a$ ± 0.009 | 0.030$^a$ ± 0.005 | 0.289$^a$ ± 0.019 | 11.68 ± 0.28 | 52.5 | 362 | a < 0.001
AspAT = Aspartate aminotransferase
AlAt = Alanine aminotransferase

TABLE 3

|  | MDA nmol/mg Protein | Free radicals nmol/mg Protein | Glutamine synthetase units/mg protein | Cysteine nmol/mg Protein | Cystine nmol/mg Protein | GSH nmol/mg Protein | NPSH nmol/mg Protein | LDH units/mg protein |
|---|---|---|---|---|---|---|---|---|
| Control $5.9 \times 10^8$ cells 100% vital | 0.130 | 0.40 | 4.09 | 0.145 | 15.08 | 17.67 | 2.07 |
| AA 1 mM $6 \times 10^8$ cells 94% vital | 0.210 | 0.41 | 3.68 | 0.130 | 14.9 | 18.90 | 1.88 |
| AA + CP 1 mM 2 mM $4 \times 10^8$ cells 97.5% vital | 0.156 | 0.41 | 11.63 | 0.79 | 17.35 | 21.32 | 2.00 |

MDA = Malonyl dialdehyde
GSH = Glutathione
NPSH = smaller substances containing sulfhydryl groups
LDH = Lactate dehydrogenase

We claim:

1. A pharmaceutical for ameliorating pain or fever in a patient, said pharmaceutical comprising 2-methyl-thiazolidine-2,4-dicarboxylic acid and paracetamol.

2. A method of ameliorating pain or fever in a patient comprising the step of:
   providing a pharmaceutical to a patient,
   wherein said pharmaceutical comprises a combination of 2-methyl-thiazolidine-2,4-dicarboxylic acid and paracetamol.

3. The method according to claim 2, further comprising the step of administrating the pharmaceutical by an oral, rectal, subcutaneous, intravenous or intramuscular route.

4. The method according to claim 2, wherein said pharmaceutical further comprises at least one compound selected from the group comprising of: an adjuvant, a binding agent, a blasting agent, a lubricant, a depot agent, a sweetening agent, an aromatizing agent, a suspending agent, and a preservative.

5. The pharmaceutical according to claim 1, further comprising at least one compound selected from the group comprising of: an adjuvant, a binding agent, a blasting agent, a lubricant, a depot agent, a sweetening agent, an aromatizing agent, a suspending agent, and a preservative.

6. The pharmaceutical according to claim 5, wherein the pharmaceutical takes the form of a preparation selected from the group consisting of: tablets, film tablets, lozenges, capsules, pills, powder, solutions or suspensions, or depot systems.

7. The pharmaceutical according to claim 5, wherein said adjuvant is selected from the group consisting of: dextrose, sugar, sorbitol, mannite, and polyvinylpyrrolidone.

8. The pharmaceutical according to claim 5, wherein said blasting agent is selected from the group consisting of: cornstarch and alginic acid.

9. The pharmaceutical according to claim 5, wherein said binding agent is selected from the group consisting of: starch and gelatin.

10. The pharmaceutical according to claim 5, wherein said lubricant is selected from the group consisting of: magnesium stearate and talc.

11. The pharmaceutical according to claim 5, wherein said depot agent is selected from the group consisting of: carboxyl polymethylene, carboxylmethyl cellulose, cellulose acetate phthalate, and polyvinyl acetate.

12. The pharmaceutical according to claim 5, wherein said sweetening agent is selected from the group consisting of: saccharin, cyclamate, and sugar.

13. The pharmaceutical according to claim 5, wherein said aromatizing agent is selected from the group consisting of: vanillin extract and orange extract.

14. The pharmaceutical according to claim 5, wherein said suspending agent comprises sodium carboxymethyl cellulose.

15. The pharmaceutical according to claim 5, wherein said preservative comprises a p-hydroxybenzoate.

* * * * *